United States Patent
Neuba et al.

(10) Patent No.: US 9,707,163 B2
(45) Date of Patent: Jul. 18, 2017

(54) REDUCTION OF AMMONIA ODOR IN AGENTS FOR DYEING AND/OR BLEACHING KERATIN FIBERS

(71) Applicant: Henkel AG & Co. KGaA, Duesseldorf (DE)

(72) Inventors: Constanze Neuba, Grevenbroich (DE); Frank Janssen, Cologne (DE)

(73) Assignee: Henkel AG & Co. KGaA (DE)

( * ) Notice: Subject to any disclaimer, the term of this patent is extended or adjusted under 35 U.S.C. 154(b) by 0 days.

(21) Appl. No.: 14/737,944

(22) Filed: Jun. 12, 2015

(65) Prior Publication Data

US 2015/0272845 A1     Oct. 1, 2015

Related U.S. Application Data

(63) Continuation of application No. PCT/EP2013/075469, filed on Dec. 4, 2013.

(30) Foreign Application Priority Data

Dec. 14, 2012 (DE) .................. 10 2012 223 202

(51) Int. Cl.
| | |
|---|---|
| *A61Q 5/10* | (2006.01) |
| *A61K 8/37* | (2006.01) |
| *A61K 8/34* | (2006.01) |
| *A61Q 5/08* | (2006.01) |
| *A61K 8/22* | (2006.01) |
| *A61K 8/23* | (2006.01) |
| *C08G 65/26* | (2006.01) |
| *C08L 71/02* | (2006.01) |

(52) U.S. Cl.
CPC ............ *A61K 8/375* (2013.01); *A61K 8/22* (2013.01); *A61K 8/23* (2013.01); *A61K 8/342* (2013.01); *A61Q 5/08* (2013.01); *A61Q 5/10* (2013.01); *C08G 65/2609* (2013.01); *C08L 71/02* (2013.01)

(58) Field of Classification Search
CPC . A61Q 5/10; A61Q 5/08; A61K 8/342; A61K 8/375; C08G 65/2609
USPC .......................................................... 8/405
See application file for complete search history.

(56) References Cited

U.S. PATENT DOCUMENTS

| | | | |
|---|---|---|---|
| 8,889,110 B2 | 11/2014 | Braida-Valerio et al. | |
| 2004/0231069 A1* | 11/2004 | Carrascal ................ | A61K 8/34 8/405 |
| 2011/0126361 A1* | 6/2011 | Manneck ............... | A61K 8/342 8/405 |

FOREIGN PATENT DOCUMENTS

| | | |
|---|---|---|
| JP | 2003-34620 A | 2/2003 |
| WO | 2011/121010 A1 | 10/2011 |

OTHER PUBLICATIONS

STIC Search Report dated Aug. 14, 2015.*
English translation (Apr. 22, 2016) of the Japanese Patent No. 2003034620 A1.*
PCT International Search Report (PCT/EP2013/075469) dated May 6, 2014.

* cited by examiner

*Primary Examiner* — Eisa Elhilo
(74) *Attorney, Agent, or Firm* — David K. Benson

(57) ABSTRACT

An agent for dyeing and/or bleaching keratin fibers, in particular human hair, including in a cosmetic carrier (a) at least one fatty alcohol selected from the group of arachyl alcohol (eicosan-1-ol), gadoleyl alcohol ((9Z)-eicos-9-en-1-ol), arachidonic alcohol ((5Z,8Z,11Z,14Z)-eicosa-5,8,11,14-tetraen-1-ol), heneicosyl alcohol (heneicosan-1-ol), behenyl alcohol (docosan-1-ol), erucyl alcohol ((13Z)-docos-13-en-1-ol) and brassidyl alcohol ((13E)-docosen-1-ol), (b) at least one persulfate salt selected from the group of ammonium persulfate, potassium persulfate and sodium persulfate, and (c) at least one glyceryl fatty acid ester of general formula (I), in which R1, R2 and R3 independently of one another stand for a hydrogen atom or a grouping of formula (II), in which R4 stands for an unbranched or branched, saturated or unsaturated $C_{11}$-$C_{28}$ alkyl group, with the proviso that at least one and at most two of the radicals selected from R1, R2 and R3 stand for a grouping of formula (II).

10 Claims, No Drawings

REDUCTION OF AMMONIA ODOR IN AGENTS FOR DYEING AND/OR BLEACHING KERATIN FIBERS

FIELD OF THE INVENTION

The present invention generally relates to the area of cosmetics and relates to agents for dyeing and/or bleaching keratinic fibers, in particular human hair, comprising in a cosmetic carrier special combinations of at least one long-chain fatty alcohol, at least one glyceryl fatty acid ester and ammonium persulfate.

BACKGROUND OF THE INVENTION

For dyeing and/or bleaching human hair, solid or pasty preparations with solid oxidation agents are usually mixed with a diluted hydrogen peroxide solution immediately prior to the application thereof. This mixture is then applied to the hair and is rinsed out again after a certain period of contact time. In order to achieve a sufficient dyeing effect, such agents are usually adjusted to be highly alkaline, the pH value is here usually between 9 and 11.5. Such high pH values are necessary in order to ensure the opening of the outer scale layer of the hair (cuticula) and to allow in this way a penetration of the active species (oxidation agent) into the hair.

In order to achieve moderate brightening effects, hydrogen peroxide is the oxidation agent of choice. However, if a stronger brightening or dyeing effect is desired, hydrogen peroxide is used together with stronger oxidation agents such as for example persulfates (sodium persulfate, potassium persulfate or ammonium persulfate).

Due to its high solubility in water, in particular the use of ammonium persulfate has proven to be advantageous in dyeing agents. Moreover, ammonia is released during the dissolution of ammonium persulfate in an alkaline medium. Apart from its effect as an alkalization agent, ammonia is additionally used for achieving bulking of the hair and as a penetration or penetration aiding agent for the species responsible for the dyeing process (such as persulfate and hydrogen peroxide).

The disadvantage of the use of ammonium persulfate is its intense pungent smell as a result of the release of ammonia. However, despite its unpleasant pungent smell, the application-related advantages associated with the use of ammonium persulfate are so manifold that ammonium persulfate is used in a large number of commercial oxidative dyeing and/or bleaching agents.

There has so far been no lack of effort to mask the ammonia odor in dyeing agents. In particular, however, the permanent minimization of odor over the entire period of application can be achieved only with great difficulty. The period of time, during which the user of dyeing agents is in contact with the dyeing agent is from the manufacturing of the application mix, via the application thereof onto the hair and the contact time up to the rinsing out of the formulation. In the case of customary contact times of 30 to 45 minutes, the entire process may take up to 90 minutes, at the most up to two hours. The masking of the odor of ammonia, which is effective over the entire period of time, constitutes the greatest challenge. It is exactly in this area that there is still a great need for optimization, and an optimal possibility for a permanent reduction of the odor of ammonia has so far not been known from the prior art.

It was therefore the object of the present invention to provide dyeing agents on the basis of the ammonium persulfate/hydrogen peroxide combination of oxide agents, which have a reduced ammonia odor. The odor-optimized agents should not suffer any loss in terms of their brightening effect.

In this context, it is in particular the object of the present invention to achieve a reduction of ammonia odor over the entire duration of application. The perception of ammonia odor should still be effectively minimized even after a contact time of up to two hours.

Surprisingly, it has been shown in the course of the works that led to the invention that it is possible to minimize the perception of ammonia odor in agents for dyeing and/or bleaching keratinic fibers effectively over the entire period of application, if apart from ammonium persulfates, certain long-chain fatty alcohols and certain glycerol fatty acid esters are added.

Furthermore, other desirable features and characteristics of the present invention will become apparent from the subsequent detailed description of the invention and the appended claims, taken in conjunction with the accompanying drawings and this background of the invention.

BRIEF SUMMARY OF THE INVENTION

An agent for dyeing and/or bleaching keratinic fibers, in particular human hair, including in a cosmetic carrier: (a) at least one fatty alcohol selected from the group of arachyl alcohol (eicosan-1-ol), gadoleyl alcohol ((9Z)-eicos-9-en-1-ol), arachidonic alcohol ((5Z,8Z,11Z,14Z)-eicosa-5,8,11,14-tetraen-1-ol), heneicosyl alcohol (heneicosan-1-ol), behenyl alcohol (docosan-1-ol), erucyl alcohol ((13Z)-docos-13-en-1-ol) and brassidyl alcohol ((13E)-docosen-1-ol); (b) ammonium persulfate as well as optionally a further persulfate salt; (c) at least one glyceryl fatty acid ester of general formula (I),

wherein
R1, R2 and R3, independently of one another, represent a hydrogen atom or a grouping of formula (II),

wherein
R4 represents an unbranched or branched, saturated or unsaturated C11-C27 alkyl group, with the proviso that at least one and no more than two of the radicals selected from R1, R2 and R3 represent a grouping of formula (II).

An agent ready to be applied for dyeing and/or bleaching keratinic fibers, in particular human hair, characterized in that it is produced immediately prior to application by mixing two preparations (A) and (B), wherein preparation (A) is an agent which (a) includes arachyl alcohol (eicosan-1-ol) and/or behenyl alcohol (docosan-1-ol) in an overall amount of 0.45 to 5.1% by weight, preferably of 0.6 to 3.9% by weight, more preferably of 0.75 to 2.7% by weight and particularly preferably of 0.9 to 1.35% by weight, in relation to the overall weight of preparation (A); and (c) includes at least one compound selected from glyceryl monostearate, glyceryl distearate, glyceryl monopalmitate and glyceryl dipalmitate in an overall amount of 0.15 to 2.7% by weight, preferably 0.3 to 2.0% by weight, more preferably of 0.4 to 1,2% by weight and particularly preferably of 0.45 to 0.9% by weight in relation to the overall weight of preparation (A), preparation (B) is an agent that includes potassium persulfate and ammonium persulfate in an overall amount of 30 to 54% by weight, preferably of 33 to 51% by weight, more preferably of 36 to 48% by weight and particularly preferably of 39 to 45% by weight in relation to the overall weight of preparation (B), and the agent ready to be applied is produced by mixing two parts by weight of preparation (A) with one part by weight of preparation (B).

DETAILED DESCRIPTION OF THE INVENTION

The following detailed description of the invention is merely exemplary in nature and is not intended to limit the invention or the application and uses of the invention. Furthermore, there is no intention to be bound by any theory presented in the preceding background of the invention or the following detailed description of the invention.

A first subject matter of the present invention is an agent for dyeing and/or bleaching keratinic fibers, in particular human hair, including in a cosmetic carrier:
(a) at least one fatty alcohol selected from the group of arachyl alcohol (eicosan-1-ol), gadoleyl alcohol ((9Z)-eicos-9-en-1-ol), arachidonic alcohol ((5Z,8Z,11Z,14Z)-eicosa-5,8,11,14-tetraen-1-ol), heneicosyl alcohol (heneicosan-1-ol), behenyl alcohol (docosan-1-ol), erucyl alcohol ((13Z)-docos-13-en-1-ol) and brassidyl alcohol ((13E)-docosen-1-ol),
(b) ammonium persulfate as well as optionally a further persulfate salt,
(c) at least one glyceryl fatty acid ester of general formula (I),

wherein
R1, R2 and R3, independently of one another, represent a hydrogen atom or a grouping of formula (II),

wherein
R4 represents an unbranched or branched, saturated or unsaturated $C_{11}$-$C_{27}$ alkyl group, with the proviso that at least one and no more than two of the radicals selected from R1, R2 and R3 represent a grouping of formula (II).

The term keratin-containing fibers is understood to mean in principle all animal hair, e.g. wool, horsehair, angora hair, fur, feathers and products or textiles made therefrom. Preferably, however, the keratinic fibers are human hair.

The term "agent for dyeing and/or bleaching" of keratinic fibers as used according to the invention is understood to mean oxidative discolouring agents that operate on the basis of oxidation agent combinations of hydrogen peroxide and persulfates. Corresponding dyeing and/or bleaching agents are not used for achieving moderate bleaching effects, but for achieving bleaching and/or dyeing effects that are as strong as possible.

The agents according to the invention include the components that are essential to the invention in a cosmetic carrier, preferably in a suitable aqueous, alcoholic or aqueous-alcoholic carrier. For the purpose of dyeing, such carriers may for example be creams, emulsions, gels, but also surfactant-containing foaming solutions such as for example shampoos, foam aerosols, foam formulations or other preparations suitable for application on hair.

Preferably, the dyeing agents according to the invention are commercially available in the form of a dyeing system on the basis of two components. The first component (preparation A) is a liquid, gel-like or creamy component including hydrogen peroxide in the cosmetic carrier as described above. The second component is preferably a solid, granulated or pasty preparation (preparation B) that includes the persulfates or the special persulfate mixtures. Immediately prior to application, preparation A and preparation B are mixed together in order to produce the dyeing agent ready for application.

As the first essential formulation component (a), the agents according to the invention for dyeing and/or bleaching keratinic fibers include at least one long-chain fatty alcohol (a) selected from the group of arachyl alcohol (eicosan-1-ol), gadoleyl alcohol ((9Z)-eicos-9-en-1-ol), arachidonic alcohol ((5Z,8Z,11Z,14Z)-eicosa-5,8,11,14-tetraen-1-ol), heneicosyl alcohol (heneicosan-1-ol), behenyl alcohol (docosan-1-ol), erucyl alcohol ((13Z)-docos-13-en-1-ol) and brassidyl alcohol ((13E)-docosen-1-ol).

These long-chain fatty alcohols (a) have a chain length of at least 20 C atoms. Within this group, special long-chain fatty alcohols have proven to be particularly suitable in respect of the odor optimization of the dyeing formulations.

In a particularly preferred embodiment, an agent for dyeing and/or bleaching keratinic fibers is characterized in that it includes arachyl alcohol (eicosan-1-ol).

In a further particularly preferred embodiment, an agent for dyeing and/or bleaching keratinic fibers is characterized in that it includes behenyl alcohol (docosan-1-ol).

In a further particularly preferred embodiment, an agent for dyeing and/or bleaching keratinic fibers is characterized in that it includes arachyl alcohol (eicosan-1-ol) and/or behenyl alcohol (docosan-1-ol).

It has further been shown that it is of advantage if the long-chain fatty alcohols (a), in particular arachyl alcohol (eicosan-1-ol) and/or behenyl alcohol (docosan-1-ol), are included in the agent according to the invention in certain volume ranges. In this connection, it has proven to be particularly preferred if the overall amount of fatty alcohol (a) is selected to be sufficiently high for an effective reduction of the ammonia odor to be achieved. On the other hand, excessively high volumes of use of fatty alcohols (a) have proven to be disadvantageous because in the latter case, the dyeing agent becomes too thick. Due to the excessively high viscosity, the diffusion of the active species (oxidation agent) into the hair shaft is prevented, which results in a degradation of the dyeing performance.

On the basis of these findings, it has proven to be particularly advantageous if the agent according to the invention includes one or more long-chain fatty alcohols (a) of the group of arachyl alcohol (eicosan-1-ol), gadoleyl alcohol ((9Z)-eicos-9-en-1-ol), arachidonic alcohol ((5Z,8Z, 11Z,14Z)-eicosa-5,8,11,14-tetraen-1-ol), heneicosyl alcohol (heneicosan-1-ol), behenyl alcohol (docosan-1-ol), erucyl alcohol ((13Z)-docos-13-en-1-ol) and brassidyl alcohol ((13E)-docosen-1-ol) in an overall amount of 0.3 to 3.4% by weight, preferably of 0.4 to 2.6% by weight, more preferably of 0.5 to 1.8% by weight and particularly preferably of 0.6 to 0.9% by weight, in relation to the overall weight of the agent ready to be applied.

In a particularly preferred embodiment, an agent according to the invention is characterized in that it includes as fatty alcohol(s) (a) arachyl alcohol (eicosan-1-ol) and/or behenyl alcohol (docosan-1-ol) in an overall amount of 0.3 to 3.4% by weight, preferably of 0.4 to 2.6% by weight, more preferably of 0.5 to 1.8% by weight and particularly preferably of 0.6 to 0.9% by weight, in relation to the overall weight of the agent ready to be applied.

Apart from the special long-chain fatty alcohols (a) having a chain length of at least 20 C atoms, the agent according to the invention may additionally also include further, shorter-chained fatty alcohols with a chain length of 12 to 18 C atoms. Suitable shorter-chained fatty alcohols with a saturated $C_{12}$-$C_{18}$ alkyl chain are for example dodecan-1-ol (dodecyl alcohol, lauryl alcohol), tetradecan-1-ol (tetradecyl alcohol, myristyl alcohol), hexadecane-1-ol (hexadecyl alcohol, cetyl alcohol, palmityl alcohol) and octadecane-1-ol (octadecyl alcohol, stearyl alcohol). A suitable shorter-chained fatty alcohol with an unsaturated $C_{12}$-$C_{18}$ alkyl chain is for example (9Z)-octadec-9-en-1-ol (oleyl alcohol).

However, in order not to excessively thicken the agent according to the invention and as a result degrade the dyeing performance, the overall amount of all the fatty alcohols included in the agent is below certain weight limits.

In a further particularly preferred embodiment, an agent according to the invention is therefore characterized in that the overall amount of all the fatty alcohols included in the agent, in relation to the overall weight of the agent ready to be applied, exceeds an amount of 5.5% by weight, preferably an amount of 4.8% by weight, more preferably an amount of 4.1% by weight and particularly preferably an amount of 3.5% by weight.

The overall amount of all the fatty alcohols included in the agent ready to be applied is understood to mean in this context the entirety of all fatty alcohols, i.e. the entirety of all the alkanols with a chain length of 8 to 40 C atoms. The basis for the calculation of the volume proportion expressed in percent by weight is here the overall weight of the agent ready to be applied.

As a second essential formulation component (b), the agents for dyeing and/or bleaching keratinic fibers according to the invention include (b) ammonium persulfate as well as optionally a further persulfate salt.

The term ammonium persulfate is understood to mean, in terms of the present invention, the persulfate with the chemical formula $(NH_4)_2S_2O_8$. Further suitable persulfate salts are for example potassium persulfate (chemical formula $K_2S_2O_8$) and sodium persulfate (chemical formula $Na_2S_2O_8$).

In the course of the works that led to the present invention it has proven to be optimal both in respect of the dyeing performance and in respect of the minimization of the ammonia odor if the agents do not include ammonium persulfate on its own, but a mixture of ammonium persulfate and potassium persulfate.

In a further preferred embodiment, an agent according to the invention is therefore characterized in that it includes ammonium persulfate and potassium persulfate. Moreover it is preferred if the persulfate(s) is/are included in the agent according to the invention in certain volume ranges.

In a further preferred embodiment, an agent according to the invention is therefore characterized in that it includes ammonium persulfate and optionally further persulfates in an overall amount of 10 to 18% by weight, preferably of 11 to 17% by weight, more preferably of 12 to 16% by weight and particularly preferably of 13 to 15% by weight, in relation to the overall weight of the agent ready to be applied.

In an especially preferred embodiment, an agent according to the invention is characterized in that it includes as persulfate salts (b) potassium persulfate and ammonium persulfate in an overall amount of 10 to 18% by weight, preferably of 11 to 17% by weight, more preferably of 12 to 16% by weight and particularly preferably of 13 to 15% by weight, in relation to the overall weight of the agent ready to be applied.

Further, the perception of ammonia odor can be minimized without any loss in dyeing performance particularly effectively and over a particularly long period of time if potassium persulfate and ammonium persulfate are used in certain volume ratios relative to each other. The indicated volume ratios are here related to the application dosages of both persulfates in the agent ready to be applied.

Preferably, potassium persulfate and ammonium persulfate are used in a weight ratio of 1:1 to 6:1 relative to each other. More preferably, potassium persulfate and ammonium persulfate are used in a weight ratio of 2:1 to 5:1 relative to each other. Especially preferably, potassium persulfate and ammonium persulfate are used in a weight ratio of 3:1 to 4:1 relative to each other. Accordingly, a particularly preferred agent is characterized in that it includes potassium persulfate and ammonium persulfate, wherein the application dosage of the potassium persulfate in the agent ready to be applied is three to four times as high as the application dosage of the ammonium persulfate.

In a further especially preferred embodiment, an agent according to the invention is characterized in that it includes as persulfate salts (b) potassium persulfate and ammonium persulfate, wherein the weight ratio between potassium persulfate and ammonium persulfate is in a range of 1:1 to 6:1, preferably of 2:1 to 5:1 and particularly preferably of 3:1 to 4:1, in relation to the overall weight of the agent ready to be applied.

As the third essential formulation component (c), the agents according to the invention include at least one glyceryl fatty acid ester of general formula (I):

wherein
R1, R2 and R3, independently of one another, represent a hydrogen atom or a grouping of formula (II):

wherein

R4 represents an unbranched or branched, saturated or unsaturated $C_{11}$-$C_{27}$ alkyl group, with the proviso that at least one and no more than two of the radicals selected from R1, R2 and R3 represent a grouping of formula (II).

Radical R4 in formula (II) represents an unbranched or branched, saturated or unsaturated $C_{11}$-$C_{27}$ alkyl group.

R4 preferably represents an unbranched, saturated $C_{11}$-$C_{27}$ alkyl group. More preferably, R4 represents an unbranched, saturated $C_{13}$-$C_{23}$ alkyl group. Particularly preferably, R4 represents an unbranched, saturated $C_{15}$-$C_{17}$ alkyl group.

In a further particularly preferred embodiment, an agent according to the invention is characterized in that it includes as the glyceryl fatty acid ester (c) of general formula (I) at least one compound of the group of formulae (Ia) to (Id):

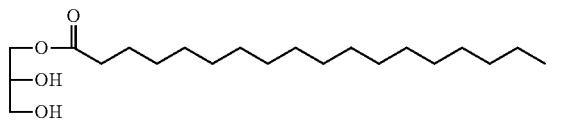
(Ia)

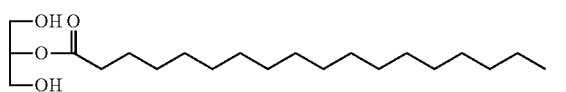
(Ib)

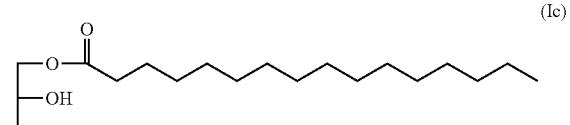
(Ic)

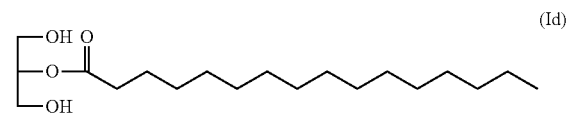
(Id)

The compounds of formulae (Ia) to (Id) are also known under the designations glyceryl monostearate and glyceryl monopalmitate.

In a further particularly preferred embodiment, an agent according to the invention is characterized in that it includes as the glyceryl fatty acid ester (c) of general formula (I) at least one compound of the croup of formulae (Ie) to (Ih):

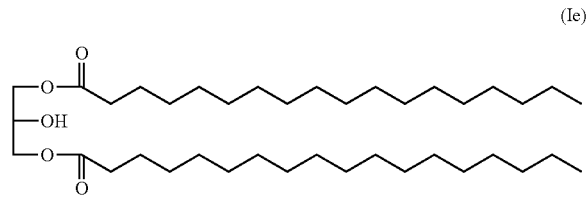
(Ie)

(If)

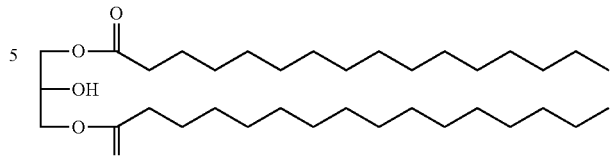
(Ig)

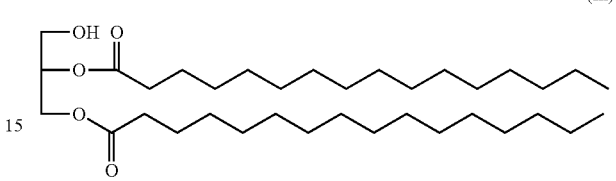
(Ih)

The compounds of formula (Ie) to (Ih) are also known under the designations glyceryl distearate and glyceryl dipalmitate.

In a particularly preferred embodiment, an agent according to the invention is characterized in that it includes as the glyceryl fatty acid ester (c) of general formula (I) at least one compound selected from formulae (Ia) to (Ih).

In a further especially preferred embodiment, an agent according to the invention is characterized in that it includes as the glyceryl fatty acid ester (c) of general formula (I) at least one compound selected from glyceryl monostearate, glyceryl distearate, glyceryl monopalmitate and glyceryl dipalmitate.

The glyceryl fatty acid esters (c) effect, in combination with the long-chain fatty alcohols (a), a reduction of the ammonia odor. The reduction in odor is particularly marked if glyceryl fatty acid esters (c) and long-chain fatty alcohols (a) are used in certain ratios relative to each other. Therefore, also the glyceryl fatty acid esters (c) are preferably included in certain amounts in the agent according to the invention.

It is particularly preferred if the agent according to the invention includes one or more glyceryl fatty acid esters (c) in an overall amount of 0.1 to 1.8% by weight, preferably of 0.2 to 1.3% by weight, more preferably of 0.25 to 0.8% by weight and particularly preferably of 0.3 to 0.6% by weight, in relation to the overall weight of the agent ready to be applied.

In a further, explicitly especially preferred embodiment, an agent according to the invention is characterized in that it includes as the glyceryl fatty acid ester (c) of general formula (I) at least one compound selected from glyceryl monostearate, glyceryl distearate, glyceryl monopalmitate and glyceryl dipalmitate in an overall amount of 0.1 to 1.8% by weight, preferably of 0.2 to 1.3% by weight, more preferably of 0.25 to 0.8% by weight and especially preferably of 0.3 to 0.6% by weight, in relation to the overall weight of the agent ready to be applied.

Under consideration of the above-mentioned preferred and particularly preferred volume ranges of the components (a), (b) and (c) that are essential to the invention, a particularly preferred agent according to the invention is characterized in that it includes, in relation to the overall weight of the agent ready to be applied, (a) 0.3 to 3.4% by weight of arachyl alcohol (eicosan-1-ol),
(b) potassium persulfate and ammonium persulfate in an overall amount of 10 to 18% by weight, and
(c) one or more compounds from the group glyceryl monostearate, glyceryl distearate, glyceryl monopalmitate and glyceryl dipalmitate in an overall amount of 0.1 to 1.8% by weight.

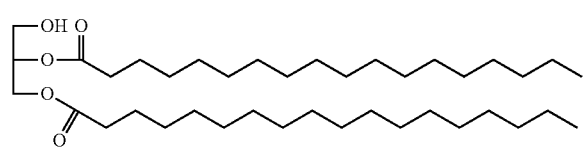

A further particularly preferred agent according to the invention is characterized in that it includes, in relation to the overall weight of the agent ready to be applied,
(a) 0.5 to 1.8% by weight of arachyl alcohol (eicosan-1-ol),
(b) potassium persulfate and ammonium persulfate in an overall amount of 10 to 18% by weight, and
(c) one or more compounds of the group of glyceryl monostearate, glyceryl distearate, glyceryl monopalmitate and glyceryl dipalmitate in an overall amount of 0.1 to 1.8% by weight.

A further particularly preferred agent according to the invention is characterized in that it includes, in relation to the overall weight of the agent ready to be applied,
(a) 0.3 to 3.4% by weight of arachyl alcohol (eicosan-1-ol),
(b) potassium persulfate and ammonium persulfate in an overall amount of 10 to 18% by weight, and
(c) one or more compounds of the group of glyceryl monostearate, glyceryl distearate, glyceryl monopalmitate and glyceryl dipalmitate in an overall amount of 0.2 to 1.3% by weight.

A further particularly preferred agent according to the invention is characterized in that it includes, in relation to the overall amount of the agent ready to be applied,
(a) 0.5 to 1.8% by weight of arachyl alcohol (eicosan-1-ol),
(b) potassium persulfate and ammonium persulfate in an overall amount of 10 to 18% by weight, and
(c) one or more compounds of the group of glyceryl monostearate, glyceryl distearate, glyceryl monopalmitate and glyceryl dipalmitate in an overall amount of 0.2 to 1.3% by weight.

A further particularly preferred agent according to the invention is characterized in that it includes, in relation to the overall weight of the agent ready to be applied,
(a) 0.3 to 3.4% by weight of arachyl alcohol (eicosan-1-ol),
(b) potassium persulfate and ammonium persulfate in an overall amount of 10 to 18% by weight, and
(c) one or more compounds of the group of glyceryl monostearate, glyceryl distearate, glyceryl monopalmitate and glyceryl dipalmitate in an overall amount of 0.25 to 0.8% by weight.

A further particularly preferred agent according to the invention is characterized in that it includes, in relation to the overall weight of the agent ready to be applied,
(a) 0.5 to 1.8% by weight of arachyl alcohol (eicosan-1-ol),
(b) potassium persulfate and ammonium persulfate in an overall amount of 10 to 18% by weight, and
(c) one or more compounds of the group of glyceryl monostearate, glyceryl distearate, glyceryl monopalmitate and glyceryl dipalmitate in an overall amount of 0.25 to 0.8% by weight.

A further particularly preferred agent according to the invention is characterized in that it includes, in relation to the overall amount of the agent ready to be applied,
(a) 0.3 to 3.4% by weight of arachyl alcohol (eicosan-1-ol),
(b) potassium persulfate and ammonium persulfate in an overall amount of 10 to 18% by weight, and
(c) one or more compounds of the group of glyceryl monostearate, glyceryl distearate, glyceryl monopalmitate and glyceryl dipalmitate in an overall amount of 0.3 to 0.6% by weight.

A further particularly preferred agent according to the invention is characterized in that it includes, in relation to the overall amount of the agent ready to be applied,
(a) 0.5 to 1.8% by weight of arachyl alcohol (eicosan-1-ol),
(b) potassium persulfate and ammonium persulfate in an overall amount of 10 to 18% by weight, and
(c) one or more compounds of the group of glyceryl monostearate, glyceryl distearate, glyceryl monopalmitate and glyceryl dipalmitate in an overall amount of 0.3 to 0.6% by weight.

A further particularly preferred agent according to the invention is characterized in that it includes, in relation to the overall amount of the agent ready to be applied,
(a) 0.3 to 3.4% by weight of arachyl alcohol (eicosan-1-ol),
(b) potassium persulfate and ammonium persulfate in an overall amount of 11 to 17% by weight, and
(c) one or more compounds of the group of glyceryl monostearate, glyceryl distearate, glyceryl monopalmitate and glyceryl dipalmitate in an overall amount of 0.1 to 1.8% by weight.

A further particularly preferred agent according to the invention is characterized in that it includes, in relation to the overall weight of the agent ready to be applied,
(a) 0.5 to 1.8% by weight of arachyl alcohol (eicosan-1-ol),
(b) potassium persulfate and ammonium persulfate in an overall amount of 11 to 17% by weight, and
(c) one or more compounds of the group of glyceryl monostearate, glyceryl distearate, glyceryl monopalmitate and glyceryl dipalmitate in an overall amount of 0.1 to 1.8% by weight.

A further particularly preferred agent according to the invention is characterized in that it includes, in relation to the overall weight of the agent ready to be applied,
(a) 0.3 to 3.4% by weight of arachyl alcohol (eicosan-1-ol),
(b) potassium persulfate and ammonium persulfate in an overall amount of 11 to 17% by weight, and
(c) one or more compounds of the group of glyceryl monostearate, glyceryl distearate, glyceryl monopalmitate and glyceryl dipalmitate in an overall amount of 0.2 to 1.3% by weight.

A further particularly preferred agent according to the invention is characterized in that it includes, in relation to the overall weight of the agent ready to be applied,
(a) 0.5 to 1.8% by weight of arachyl alcohol (eicosan-1-ol),
(b) potassium persulfate and ammonium persulfate in an overall amount of 11 to 17% by weight, and
(c) one or more compounds of the group of glyceryl monostearate, glyceryl distearate, glyceryl monopalmitate and glyceryl dipalmitate in an overall amount of 0.2 to 1.3% by weight.

A further particularly preferred agent according to the invention is characterized in that it includes, in relation to the overall weight of the agent ready to be applied,
(a) 0.3 to 3.4% by weight of arachyl alcohol (eicosan-1-ol),
(b) potassium persulfate and ammonium persulfate in an overall amount of 11 to 17% by weight, and
(c) one or more compounds of the group of glyceryl monostearate, glyceryl distearate, glyceryl monopalmitate and glyceryl dipalmitate in an overall amount of 0.25 to 0.8% by weight.

A further particularly preferred agent according to the invention is characterized in that it includes, in relation to the overall weight of the agent ready to be applied,
(a) 0.5 to 1.8% by weight of arachyl alcohol (eicosan-1-ol),
(b) potassium persulfate and ammonium persulfate in an overall amount of 11 to 17% by weight, and
(c) one or more compounds of the group of glyceryl monostearate, glyceryl distearate, glyceryl monopalmitate and glyceryl dipalmitate in an overall amount of 0.25 to 0.8% by weight.

A further particularly preferred agent according to the invention is characterized in that it includes, in relation to the overall weight of the agent ready to be applied, (a) 0.3 to 3.4% of arachyl alcohol (eicosan-1-ol),
(b) potassium persulfate and ammonium persulfate in an overall amount of 11 to 17% by weight, and
(c) one or more compounds of the group of glyceryl monostearate, glyceryl distearate, glyceryl monopalmitate and glyceryl dipalmitate in an overall amount of 0.3 to 0.6% by weight.

A further particularly preferred agent according to the invention is characterized in that it includes, in relation to the overall weight of the agent ready to be applied,
(a) 0.5 to 1.8% by weight of arachyl alcohol (eicosan-1-ol),
(b) potassium persulfate and ammonium persulfate in an overall amount of 11 to 17% by weight, and
(c) one or more compounds of the group of glyceryl monostearate, glyceryl distearate, glyceryl monopalmitate and glyceryl dipalmitate in an overall amount of 0.3 to 0.6% by weight.

A further particularly preferred agent according to the invention is characterized in that it includes, in relation to the overall weight of the agent ready to be applied,
(a) 0.3 to 3.4% by weight of arachyl alcohol (eicosan-1-ol),
(b) potassium persulfate and ammonium persulfate in an overall amount of 12 to 16% by weight, and
(c) one or more compounds of the group of glyceryl monostearate, glyceryl distearate, glyceryl monopalmitate and glyceryl dipalmitate in an overall amount of 0.1 to 1.8% by weight.

A further particularly preferred agent according to the invention is characterized in that it includes, in relation to the overall weight of the agent ready to be applied,
(a) 0.5 to 1.8% by weight of arachyl alcohol (eicosan-1-ol),
(b) potassium persulfate and ammonium persulfate in an overall amount of 12 to 16% by weight, and
(c) one or more compounds of the group of glyceryl monostearate, glyceryl distearate, glyceryl monopalmitate and glyceryl dipalmitate in an overall amount of 0.1 to 1.8% by weight.

A further particularly preferred agent according to the invention is characterized in that it includes, in relation to the overall weight of the agent ready to be applied,
(a) 0.3 to 3.4% by weight of arachyl alcohol (eicosan-1-ol),
(b) potassium persulfate and ammonium persulfate in an overall amount of 12 to 16% by weight, and
(c) one or more compounds of the group of glyceryl monostearate, glyceryl distearate, glyceryl monopalmitate and glyceryl dipalmitate in an overall amount of 0.2 to 1.3% by weight.

A further particularly preferred agent according to the invention is characterized in that it includes, in relation to the overall weight of the agent ready to be applied,
(a) 0.5 to 1.8% by weight of arachyl alcohol (eicosan-1-ol),
(b) potassium persulfate and ammonium persulfate in an overall amount of 12 to 16% by weight, and
(c) one or more compounds of the group of glyceryl monostearate, glyceryl distearate, glyceryl monopalmitate and glyceryl dipalmitate in an overall amount of 0.2 to 1.3% by weight.

A further particularly preferred agent according to the invention is characterized in that it includes, in relation to the overall weight of the agent ready to be applied,
(a) 0.3 to 3.4% by weight of arachyl alcohol (eicosan-1-ol),
(b) potassium persulfate and ammonium persulfate in an overall amount of 12 to 16% by weight, and
(c) one or more compounds of the group of glyceryl monostearate, glyceryl distearate, glyceryl monopalmitate and glyceryl dipalmitate in an overall amount of 0.25 to 0.8% by weight.

A further particularly preferred agent according to the invention is characterized in that it includes, in relation to the overall weight of the agent ready to be applied,
(a) 0.5 to 1.8% by weight of arachyl alcohol (eicosan-1-ol),
(b) potassium persulfate and ammonium persulfate in an overall amount of 12 to 16% by weight, and
(c) one or more compounds of the group of glyceryl monostearate, glyceryl distearate, glyceryl monopalmitate and glyceryl dipalmitate in an overall amount of 0.25 to 0.8% by weight.

A further particularly preferred agent according to the invention is characterized in that it includes, in relation to the overall weight of the agent ready to be applied,
(a) 0.3 to 3.4% by weight of arachyl alcohol (eicosan-1-ol),
(b) potassium persulfate and ammonium persulfate in an overall amount of 12 to 16% by weight, and
(c) one or more compounds of the group of glyceryl monostearate, glyceryl distearate, glyceryl monopalmitate and glyceryl dipalmitate in an overall amount of 0.3 to 0.6% by weight.

A further particularly preferred agent according to the invention is characterized in that it includes, in relation to the overall weight of the agent ready to be applied,
(a) 0.5 to 1.8% by weight of arachyl alcohol (eicosan-1-ol),
(b) potassium persulfate and ammonium persulfate in an overall amount of 12 to 16% by weight, and
(c) one or more compounds of the group of glyceryl monostearate, glyceryl distearate, glyceryl monopalmitate and glyceryl dipalmitate in an overall amount of 0.3 to 0.6% by weight.

A further particularly preferred agent according to the invention is characterized in that it includes, in relation to the overall weight of the agent ready to be applied,
(a) 0.3 to 3.4% by weight of arachyl alcohol (eicosan-1-ol),
(b) potassium persulfate and ammonium persulfate in an overall amount of 13 to 15% by weight, and
(c) one or more compounds of the group of glyceryl monostearate, glyceryl distearate, glyceryl monopalmitate and glyceryl dipalmitate in an overall amount of 0.1 to 1.8% by weight.

A further particularly preferred agent according to the invention is characterized in that it includes, in relation to the overall weight of the agent ready to be applied,
(a) 0.4 to 2.6% by weight of arachyl alcohol (eicosan-1-ol),
(b) potassium persulfate and ammonium persulfate in an overall amount of 13 to 15% by weight, and
(c) one or more compounds of the group of glyceryl monostearate, glyceryl distearate, glyceryl monopalmitate and glyceryl dipalmitate in an overall amount of 0.1 to 1.8% by weight.

A further particularly preferred agent according to the invention is characterized in that it includes, in relation to the overall weight of the agent ready to be applied,
(a) 0.6 to 0.9% by weight of arachyl alcohol (eicosan-1-ol),
(b) potassium persulfate and ammonium persulfate in an overall amount of 13 to 15% by weight, and
(c) one or more compounds of the group of glyceryl monostearate, glyceryl distearate, glyceryl monopalmitate and glyceryl dipalmitate in an overall amount of 0.1 to 1.8% by weight.

A further particularly preferred agent according to the invention is characterized in that it includes, in relation to the overall weight of the agent ready to be applied,
(a) 0.4 to 2.6% by weight of arachyl alcohol (eicosan-1-ol),
(b) potassium persulfate and ammonium persulfate in an overall amount of 13 to 15% by weight, and (c) one or more compounds of the group of glyceryl monostearate, glyceryl distearate, glyceryl monopalmitate and glyceryl dipalmitate in an overall amount of 0.2 to 1.3% by weight.

A further particularly preferred agent according to the invention is characterized in that it includes, in relation to the overall weight of the agent ready to be applied,
(a) 0.6 to 0.9% by weight of arachyl alcohol (eicosan-1-ol),
(b) potassium persulfate and ammonium persulfate in an overall amount of 13 to 15% by weight, and
(c) one or more compounds of the group of glyceryl monostearate, glyceryl distearate, glyceryl monopalmitate and glyceryl dipalmitate in an overall amount of 0.2 to 1.3% by weight.

A further particularly preferred agent according to the invention is characterized in that it includes, in relation to the overall weight of the agent ready to be applied,
(a) 0.4 to 2.6% by weight of arachyl alcohol (eicosan-1-ol),
(b) potassium persulfate and ammonium persulfate in an overall amount of 13 to 15% by weight, and
(c) one or more compounds of the group of glyceryl monostearate, glyceryl distearate, glyceryl monopalmitate and glyceryl dipalmitate in an overall amount of 0.25 to 0.8% by weight.

A further particularly preferred agent according to the invention is characterized in that it includes, in relation to the overall weight of the agent ready to be applied,
(a) 0.6 to 0.9% by weight of arachyl alcohol (eicosan-1-ol),
(b) potassium persulfate and ammonium persulfate in an overall amount of 13 to 15% by weight, and
(c) one or more compounds of the group of glyceryl monostearate, glyceryl distearate, glyceryl monopalmitate and glyceryl dipalmitate in an overall amount of 0.25 to 0.8% by weight.

A further particularly preferred agent according to the invention is characterized in that it includes, in relation to the overall weight of the agent ready to be applied,
(a) 0.4 to 2.6% by weight of arachyl alcohol (eicosan-1-ol),
(b) potassium persulfate and ammonium persulfate in an overall amount of 13 to 15% by weight, and
(c) one or more compounds of the group of glyceryl monostearate, glyceryl distearate, glyceryl monopalmitate and glyceryl dipalmitate in an overall amount of 0.3 to 0.6% by weight.

A further particularly preferred agent according to the invention is characterized in that it includes, in relation to the overall weight of the agent ready to be applied,
(a) 0.6 to 0.9% by weight of arachyl alcohol (eicosan-1-ol),
(b) potassium persulfate and ammonium persulfate in an overall amount of 13 to 15% by weight, and
(c) one or more compounds of the group of glyceryl monostearate, glyceryl distearate, glyceryl monopalmitate and glyceryl dipalmitate in an overall amount of 0.3 to 0.6% by weight.

A further particularly preferred agent according to the invention is characterized in that it includes, in relation to the overall weight of the agent ready to be applied,
(a) 0.4 to 2.6% by weight of behenyl alcohol (docosan-1-ol),
(b) potassium persulfate and ammonium persulfate in an overall amount of 10 to 18% by weight, and
(c) one or more compounds of the group of glyceryl monostearate, glyceryl distearate, glyceryl monopalmitate and glyceryl dipalmitate in an overall amount of 0.1 to 1.8% by weight.

A further particularly preferred agent according to the invention is characterized in that it includes, in relation to the overall weight of the agent ready to be applied,
(a) 0.6 to 0.9% by weight of behenyl alcohol (docosan-1-ol),
(b) potassium persulfate and ammonium persulfate in an overall amount of 10 to 18% by weight, and
(c) one or more compounds of the group of glyceryl monostearate, glyceryl distearate, glyceryl monopalmitate and glyceryl dipalmitate in an overall amount of 0.1 to 1.8% by weight.

A further particularly preferred agent according to the invention is characterized in that it includes, in relation to the overall weight of the agent ready to be applied,
(a) 0.4 to 2.6% by weight of behenyl alcohol (docosan-1-ol),
(b) potassium persulfate and ammonium persulfate in an overall amount of 10 to 18% by weight, and
(c) one or more compounds of the group of glyceryl monostearate, glyceryl distearate, glyceryl monopalmitate and glyceryl dipalmitate in an overall amount of 0.2 to 1.3% by weight.

A further particularly preferred agent according to the invention is characterized in that it includes, in relation to the overall weight of the agent ready to be applied,
(a) 0.6 to 0.9% by weight of behenyl alcohol (docosan-1-ol),
(b) potassium persulfate and ammonium persulfate in an overall amount of 10 to 18% by weight, and
(c) one or more compounds of the group of glyceryl monostearate, glyceryl distearate, glyceryl monopalmitate and glyceryl dipalmitate in an overall amount of 0.2 to 1.3% by weight.

A further particularly preferred agent according to the invention is characterized in that it includes, in relation to the overall weight of the agent ready to be applied,
(a) 0.4 to 2.6% by weight of behenyl alcohol (docosan-1-ol),
(b) potassium persulfate and ammonium persulfate in an overall amount of 10 to 18% by weight, and
(c) one or more compounds of the group of glyceryl monostearate, glyceryl distearate, glyceryl monopalmitate and glyceryl dipalmitate in an overall amount of 0.25 to 0.8% by weight.

A further particularly preferred agent according to the invention is characterized in that it includes, in relation to the overall weight of the agent ready to be applied,
(a) 0.6 to 0.9% by weight of behenyl alcohol (docosan-1-ol),
(b) potassium persulfate and ammonium persulfate in an overall amount of 10 to 18% by weight, and
(c) one or more compounds of the group of glyceryl monostearate, glyceryl distearate, glyceryl monopalmitate and glyceryl dipalmitate in an overall amount of 0.25 to 0.8% by weight.

A further particularly preferred agent according to the invention is characterized in that it includes, in relation to the overall weight of the agent ready to be applied,
(a) 0.4 to 2.6% by weight of behenyl alcohol (docosan-1-ol),
(b) potassium persulfate and ammonium persulfate in an overall amount of 10 to 18% by weight, and
(c) one or more compounds of the group of glyceryl monostearate, glyceryl distearate, glyceryl monopalmitate and glyceryl dipalmitate in an overall amount of 0.3 to 0.6% by weight.

A further particularly preferred agent according to the invention is characterized in that it includes, in relation to the overall weight of the agent ready to be applied,
(a) 0.6 to 0.9% by weight of behenyl alcohol (docosan-1-ol),
(b) potassium persulfate and ammonium persulfate in an overall amount of 10 to 18% by weight, and
(c) one or more compounds of the group of glyceryl monostearate, glyceryl distearate, glyceryl monopalmitate and glyceryl dipalmitate in an overall amount of 0.3 to 0.6% by weight.

A further particularly preferred agent according to the invention is characterized in that it includes, in relation to the overall weight of the agent ready to be applied,
(a) 0.4 to 2.6% by weight of behenyl alcohol (docosan-1-ol),
(b) potassium persulfate and ammonium persulfate in an overall amount of 11 to 17% by weight, and
(c) one or more compounds of the group of glyceryl monostearate, glyceryl distearate, glyceryl monopalmitate and glyceryl dipalmitate in an overall amount of 0.1 to 1.8% by weight.

A further particularly preferred agent according to the invention is characterized in that it includes, in relation to the overall weight of the agent ready to be applied,
(a) 0.6 to 0.9% by weight of behenyl alcohol (docosan-1-ol),
(b) potassium persulfate and ammonium persulfate in an overall amount of 11 to 17% by weight, and
(c) one or more compounds of the group of glyceryl monostearate, glyceryl distearate, glyceryl monopalmitate and glyceryl dipalmitate in an overall amount of 0.1 to 1.8% by weight.

A further particularly preferred agent according to the invention is characterized in that it includes, in relation to the overall weight of the agent ready to be applied,
(a) 0.4 to 2.6% by weight of behenyl alcohol (docosan-1-ol),
(b) potassium persulfate and ammonium persulfate in an overall amount of 11 to 17% by weight, and
(c) one or more compounds of the group of glyceryl monostearate, glyceryl distearate, glyceryl monopalmitate and glyceryl dipalmitate in an overall amount of 0.2 to 1.3% by weight.

A further particularly preferred agent according to the invention is characterized in that it includes, in relation to the overall weight of the agent ready to be applied,
(a) 0.6 to 0.9% by weight of behenyl alcohol (docosan-1-ol),
(b) potassium persulfate and ammonium persulfate in an overall amount of 11 to 17% by weight, and
(c) one or more compounds of the group of glyceryl monostearate, glyceryl distearate, glyceryl monopalmitate and glyceryl dipalmitate in an overall amount of 0.2 to 1.3% by weight.

A further particularly preferred agent according to the invention is characterized in that it includes, in relation to the overall weight of the agent ready to be applied,
(a) 0.4 to 2.6% by weight of behenyl alcohol (docosan-1-ol),
(b) potassium persulfate and ammonium persulfate in an overall amount of 11 to 17% by weight, and
(c) one or more compounds of the group of glyceryl monostearate, glyceryl distearate, glyceryl monopalmitate and glyceryl dipalmitate in an overall amount of 0.25 to 0.8% by weight.

A further particularly preferred agent according to the invention is characterized in that it includes, in relation to the overall weight of the agent ready to be applied,
(a) 0.6 to 0.9% by weight of behenyl alcohol (docosan-1-ol),
(b) potassium persulfate and ammonium persulfate in an overall amount of 11 to 17% by weight, and
(c) one or more compounds of the group of glyceryl monostearate, glyceryl distearate, glyceryl monopalmitate and glyceryl dipalmitate in an overall amount of 0.25 to 0.8% by weight.

A further particularly preferred agent according to the invention is characterized in that it includes, in relation to the overall weight of the agent ready to be applied,
(a) 0.4 to 2.6% by weight of behenyl alcohol (docosan-1-ol),
(b) potassium persulfate and ammonium persulfate in an overall amount of 11 to 17% by weight, and
(c) one or more compounds of the group of glyceryl monostearate, glyceryl distearate, glyceryl monopalmitate and glyceryl dipalmitate in an overall amount of 0.3 to 0.6% by weight.

A further particularly preferred agent according to the invention is characterized in that it includes, in relation to the overall weight of the agent ready to be applied,
(a) 0.6 to 0.9% by weight of behenyl alcohol (docosan-1-ol),
(b) potassium persulfate and ammonium persulfate in an overall amount of 11 to 17% by weight, and
(c) one or more compounds of the group of glyceryl monostearate, glyceryl distearate, glyceryl monopalmitate and glyceryl dipalmitate in an overall amount of 0.3 to 0.6% by weight.

A further particularly preferred agent according to the invention is characterized in that it includes, in relation to the overall weight of the agent ready to be applied,
(a) 0.4 to 2.6% by weight of behenyl alcohol (docosan-1-ol),
(b) potassium persulfate and ammonium persulfate in an overall amount of 12 to 16% by weight, and
(c) one or more compounds of the group of glyceryl monostearate, glyceryl distearate, glyceryl monopalmitate and glyceryl dipalmitate in an overall amount of 0.1 to 1.8% by weight.

A further particularly preferred agent according to the invention is characterized in that it includes, in relation to the overall weight of the agent ready to be applied,
(a) 0.6 to 0.9% by weight of behenyl alcohol (docosan-1-ol),
(b) potassium persulfate and ammonium persulfate in an overall amount of 12 to 16% by weight, and
(c) one or more compounds of the group of glyceryl monostearate, glyceryl distearate, glyceryl monopalmitate and glyceryl dipalmitate in an overall amount of 0.1 to 1.8% by weight.

A further particularly preferred agent according to the invention is characterized in that it includes, in relation to the overall weight of the agent ready to be applied,
(a) 0.4 to 2.6% by weight of behenyl alcohol (docosan-1-ol),
(b) potassium persulfate and ammonium persulfate in an overall amount of 12 to 16% by weight, and
(c) one or more compounds of the group of glyceryl monostearate, glyceryl distearate, glyceryl monopalmitate and glyceryl dipalmitate in an overall amount of 0.2 to 1.3% by weight.

A further particularly preferred agent according to the invention is characterized in that it includes, in relation to the overall weight of the agent ready to be applied,
(a) 0.6 to 0.9% by weight of behenyl alcohol (docosan-1-ol),
(b) potassium persulfate and ammonium persulfate in an overall amount of 12 to 16% by weight, and
(c) one or more compounds of the group of glyceryl monostearate, glyceryl distearate, glyceryl monopalmitate and glyceryl dipalmitate in an overall amount of 0.2 to 1.3% by weight.

A further particularly preferred agent according to the invention is characterized in that it includes, in relation to the overall weight of the agent ready to be applied,
(a) 0.4 to 2.6% by weight of behenyl alcohol (docosan-1-ol),
(b) potassium persulfate and ammonium persulfate in an overall amount of 12 to 16% by weight, and
(c) one or more compounds of the group of glyceryl monostearate, glyceryl distearate, glyceryl monopalmitate and glyceryl dipalmitate in an overall amount of 0.25 to 0.8% by weight.

A further particularly preferred agent according to the invention is characterized in that it includes, in relation to the overall weight of the agent ready to be applied, (a) 0.6 to 0.9% by weight of behenyl alcohol (docosan-1-ol),
(b) potassium persulfate and ammonium persulfate in an overall amount of 12 to 16% by weight, and
(c) one or more compounds of the group of glyceryl monostearate, glyceryl distearate, glyceryl monopalmitate and glyceryl dipalmitate in an overall amount of 0.25 to 0.8% by weight.

A further particularly preferred agent according to the invention is characterized in that it includes, in relation to the overall weight of the agent ready to be applied,
(a) 0.4 to 2.6% by weight of behenyl alcohol (docosan-1-ol),
(b) potassium persulfate and ammonium persulfate in an overall amount of 12 to 16% by weight, and
(c) one or more compounds of the group of glyceryl monostearate, glyceryl distearate, glyceryl monopalmitate and glyceryl dipalmitate in an overall amount of 0.3 to 0.6% by weight.

A further particularly preferred agent according to the invention is characterized in that it includes, in relation to the overall weight of the agent ready to be applied,
(a) 0.6 to 0.9% by weight of behenyl alcohol (docosan-1-ol),
(b) potassium persulfate and ammonium persulfate in an overall amount of 12 to 16% by weight, and
(c) one or more compounds of the group of glyceryl monostearate, glyceryl distearate, glyceryl monopalmitate and glyceryl dipalmitate in an overall amount of 0.3 to 0.6% by weight.

A further particularly preferred agent according to the invention is characterized in that it includes, in relation to the overall weight of the agent ready to be applied,
(a) 0.4 to 2.6% by weight of behenyl alcohol (docosan-1-ol),
(b) potassium persulfate and ammonium persulfate in an overall amount of 13 to 15% by weight, and
(c) one or more compounds of the group of glyceryl monostearate, glyceryl distearate, glyceryl monopalmitate and glyceryl dipalmitate in an overall amount of 0.1 to 1.8% by weight.

A further particularly preferred agent according to the invention is characterized in that it includes, in relation to the overall weight of the agent ready to be applied,
(a) 0.6 to 0.9% by weight of behenyl alcohol (docosan-1-ol),
(b) potassium persulfate and ammonium persulfate in an overall amount of 13 to 15% by weight, and
(c) one or more compounds of the group of glyceryl monostearate, glyceryl distearate, glyceryl monopalmitate and glyceryl dipalmitate in an overall amount of 0.1 to 1.8% by weight.

A further particularly preferred agent according to the invention is characterized in that it includes, in relation to the overall weight of the agent ready to be applied,
(a) 0.4 to 2.6% by weight of behenyl alcohol (docosan-1-ol),
(b) potassium persulfate and ammonium persulfate in an overall amount of 13 to 15% by weight, and
(c) one or more compounds of the group of glyceryl monostearate, glyceryl distearate, glyceryl monopalmitate and glyceryl dipalmitate in an overall amount of 0.2 to 1.3% by weight.

A further particularly preferred agent according to the invention is characterized in that it includes, in relation to the overall weight of the agent ready to be applied,
(a) 0.5 to 1.8% by weight of behenyl alcohol (docosan-1-ol),
(b) potassium persulfate and ammonium persulfate in an overall amount of 13 to 15% by weight, and
(c) one or more compounds of the group of glyceryl monostearate, glyceryl distearate, glyceryl monopalmitate and glyceryl dipalmitate in an overall amount of 0.2 to 1.3% by weight.

A further particularly preferred agent according to the invention is characterized in that it includes, in relation to the overall weight of the agent ready to be applied,
(a) 0.3 to 3.4% by weight of behenyl alcohol (docosan-1-ol),
(b) potassium persulfate and ammonium persulfate in an overall amount of 13 to 15% by weight, and
(c) one or more compounds of the group of glyceryl monostearate, glyceryl distearate, glyceryl monopalmitate and glyceryl dipalmitate in an overall amount of 0.25 to 0.8% by weight.

A further particularly preferred agent according to the invention is characterized in that it includes, in relation to the overall weight of the agent ready to be applied
(a) 0.6 to 0.9% by weight of behenyl alcohol (docosan-1-ol),
(b) potassium persulfate and ammonium persulfate in an overall amount of 13 to 15% by weight, and
(c) one or more compounds of the group of glyceryl monostearate, glyceryl distearate, glyceryl monopalmitate and glyceryl dipalmitate in an overall amount of 0.25 to 0.8% by weight.

A further particularly preferred agent according to the invention is characterized in that it includes, in relation to the overall weight of the agent ready to be applied,
(a) 0.3 to 3.4% by weight of behenyl alcohol (docosan-1-ol),
(b) potassium persulfate and ammonium persulfate in an overall amount of 13 to 15% by weight, and
(c) one or more compounds of the group of glyceryl monostearate, glyceryl distearate, glyceryl monopalmitate and glyceryl dipalmitate in an overall amount of 0.3 to 0.6% by weight.

A further particularly preferred agent according to the invention is characterized in that it includes, in relation to the overall weight of the agent ready to be applied,
(a) 0.6 to 0.9% by weight of behenyl alcohol (docosan-1-ol),
(b) potassium persulfate and ammonium persulfate in an overall amount of 13 to 15% by weight, and
(c) one or more compounds of the group of glyceryl monostearate, glyceryl distearate, glyceryl monopalmitate and glyceryl dipalmitate in an overall amount of 0.3 to 0.6% by weight.

In the course of the works that led to the present invention it has further been shown that the object of the invention can be completely and satisfactorily achieved in particular if the agents according to the invention include further selected formulation components. Particularly preferably, the agents additionally include at least one or more amphoteric and/or zwitterionic surfactants.

Surfactants are amphiphilic (bifunctional) compounds consisting of at least one hydrophobic and at least one hydrophilic molecule component. The hydrophobic residue is preferably a hydrocarbon chain with 8-28 carbon atoms, which may be saturated or unsaturated, linear or branched. Particularly preferably, this $C_8$-$C_{28}$ alkyl chain is linear.

Basic properties of the surfactants are the orientated absorption on the interfaces as well as the aggregation into micelles and the formation of lyotropic phases.

The amphoteric surfactants are subdivided into ampholytic surfactants and zwitterionic surfactants. Ampholytic surfactants are understood to be such surface active compounds which have both acidic (for example —COOH or —SO$_3$H groups) and basic hydrophilic groups (for example amino groups) and will therefore, depending on the conditions, show an acidic or basic behaviour. Zwitterionic surfactants will be understood by a person skilled in the art to be surfactants that carry both a negative and a positive charge in the same molecule.

Examples of preferred zwitterionic surfactants are betaines, the N-alkyl-N,N-dimethyl-ammonium-glycinates, the N-acyl-aminopropyl-N,N-dimethyl-ammonium-glycinates and the 2-alkyl-3-carboxymethyl-3-hydroxyethyl-imidazolines each having 8 to 24 C atoms in the alkyl group.

Examples of preferred ampholytic surfactants are N-alkylglycines, N-alkylamino propionic acids, N-alkyl amino butyric acids, N-alkylimino dipropionic acids, N-hydroxyethyl-N-alkylamido propyl glycine, N-alkyltaurine, N-alkylsarcosine, 2-alkylamino propionic acids and alkylamino acetic acids each having 8 to 24 C atoms in the alkyl group.

In order to achieve the object of the invention, particularly suitable amphoteric and/or zwitterionic surfactants are those compounds that are known under the INCI designation of disodium coco-amphodipropionate.

In order to achieve the object of the invention, particularly suitable amphoteric and/or zwitterionic surfactants are further those compounds that are known under the INCI designation coco-amidopropyl betaine.

The agents according to the invention include the amphoteric and/or zwitterionic surfactants preferably in specific volume ranges. Preferably, the agents additionally include one or more amphoteric and/or zwitterionic surfactants in an overall amount of 0.01 to 0.5% by weight, preferably of 0.03 to 0.4% by weight, more preferably of 0.05 to 0.3% by weight and particularly preferably of 0.07 to 0.2% by weight, in relation to the overall weight of the agent ready to be applied.

Accordingly, in a further particularly preferred embodiment, an agent according to the invention is characterized in that it additionally includes one or more amphoteric and/or zwitterionic surfactants in an overall amount of 0.01 to 0.5% by weight, preferably of 0.03 to 0.4% by weight, more preferably of 0.05 to 0.3% by weight and particularly preferably of 0.07 to 0.2% by weight, in relation to the overall weight of the agent ready to be applied.

The addition of one or more amphoteric and/or zwitterionic surfactants can further enhance the odor characteristics of the dyeing or bleaching agents. It has unexpectedly been shown in this context that a further minimization of the ammonia odor will not generally occur with the addition of just any type of surfactant. The addition of anionic surfactants surprisingly causes a deterioration of the odor properties of the agents according to the invention again, because the ammonia odor is slightly intensified again if anionic surfactants are added.

In a preferred embodiment, the agents according to the invention are therefore free of anionic surfactants. Anionic surfactants are understood in this context to be surfactants with exclusively anionic charges.

In a further particularly preferred embodiment, an agent for dyeing and/or brightening keratinic fibers is therefore characterized in that it includes, in relation to the overall weight of the agent ready to be applied, less than 0.5% by weight, preferably less than 0.3% by weight, more preferably less than 0.1% by weight of anionic surfactants and particularly preferably no anionic surfactants.

As a further additional formulation component, the agents according to the invention may additionally include at least one ethoxylated fatty alcohol of formula (III) with a degree of ethoxylation of at least 25.

Ethoxylation (also oxyethylation) is understood to be the reaction of the fatty alcohols with ethylene oxide (EO). By inserting at least 25 groupings of the type —CH2-CH2-O— per molecule of fatty alcohol, linear polyethers develop which carry on one end of the chain a hydroxy group and on the other end of the chain the $C_8$-$C_{28}$ alkyl group of the fatty alcohol.

In a further particularly preferred embodiment, an agent according to the invention is characterized in that it additionally includes one or more ethoxylated fatty alcohols of formula (III),

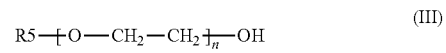

(III)

wherein R5 represents an unbranched or branched, saturated or unsaturated $C_{12}$-$C_{28}$ alkyl group, preferably for a saturated, unbranched $C_{16}$ or $C_{18}$ alkyl group, n represents an integer of 25 to 120, preferably an integer of 25 to 80, more preferably an integer of 25 to 50 and particularly preferably an integer of 25 to 35.

An especially preferred ethoxylated fatty alcohol of formula (III) is Ceteareth-30.

The ethoxylated fatty alcohol(s) of formula (III) may be included in the agents in an overall amount of 0.1 to 2.0% by weight, preferably of 0.2 to 1.6% by weight, more preferably of 0.3 to 1.2% by weight and particularly preferably of 0.3 to 0.6% by weight, in relation to the overall weight of the agent ready to be applied.

Moreover, it has proven to be particularly advantageous if the agents according to the invention additionally include at least one carbohydrate compound. In particular, Paraffinium Liquidum has proven to be suitable in this context.

In a further preferred embodiment, an agent according to the invention is therefore characterized in that it includes, in relation to the overall weight of the agent ready to be applied, 0.5 to 4.5% by weight, preferably 1.0 to 4.0% by weight, more preferably 1.25 to 3.0% by weight and particularly preferably 1.50 to 2.0% by weight of Paraffinium Liquidum.

As has already been described, the agents according to the invention are agents for dyeing and/or bleaching keratinic fibers, which agents, in a preferred embodiment, do not include any dyes.

For varying the shade of blonde obtained with the agents, however, it may under certain circumstances be necessary to add small amounts of oxidation dye precursors and/or substantive dyes to the agents.

Oxidation dye precursors include oxidation dye precursors of the developer type and of the coupler type. Particularly suitable oxidation dye precursors of the developer type are here selected from at least one compound of the group of p-phenylenediamine, p-toluylenediamine, 2-(2-hydroxyethyl)-p-phenylenediamine, 2-(1,2-dihydroxyethyl)-p-phenylenediamine, N,N-Bis-(2-hydroxyethyl)-p-phenylenediamine, 2-methoxymethyl-p-phenylenediamine, N-(4-amino-3-methylphenyl)-N-[3-(1H-imidazol-1-yl)-propyl]amine, N,N'-Bis-(2-hydroxyethyl)-N,N'-bis-(4-aminophenyl)-1,3-diamino-propane-2-ol, Bis-(2-hydroxy-5-aminophenyl)methane, 1,3-Bis-(2,5-diaminophenoxyl)propane-2-ol, N,N'-Bis-(4-aminophenyl)-1,4-diazacycloheptane, 1,10-Bis-(2,5-diaminophenyl)-1,4,7,10-tetraoxadecane, p-aminophenol, 4-amino-3-methylphenol, 4-amino-2-aminomethylphenol, 4-amino-2-(1,2-dihydroxyethyl)phenol, 4-amino-2-(diethylaminomethyl)phenol, 4,5-diamino-1-(2-hydroxyethyl)pyrazol, 2,4,5,6-tetraaminopyrimidine, 4-hydroxy-2,5,6-triaminopyrimidine, 2-hydroxy-4,5,6-triaminopyrimidine, 2,3-diamino-6,7-dihydro-1H,5H-pyrazolo [1,2-a]pyrazol-1-one as well as the physiologically acceptable salts thereof.

Particularly suitable oxidation dye precursors of the coupler type are selected from the group of 3-aminophenol, 5-amino-2-methylphenol, 3-amino-2-chloro-6-methylphenol, 2-hydroxy-4-aminophenoxyethanol, 5-amino-4-chloro-2-methylphenol, 5-(2-hydroxyethyl)-amino-2-methylphenol, 2,4-dichloro-3-aminophenol, 2-aminophenol, 3-phenylenediamine, 2-(2,4-diaminophenoxyl)ethanol, 1,3-Bis(2,4-diaminophenoxy)propane, 1-methoxy-2-amino-4-(2-hydroxyethylamino)benzene, 1,3-Bis(2,4-diaminophenyl)propane, 2,6-Bis(2'-hydroxyethylamino)-1-methylbenzene, 2-({3-[(2-hydroxyethyl)amino]-4-methoxy-5-methylphenyl}amino)ethanol, 2-({3-[(2-hydroxyethyl)amino]-2-methoxy-5-methylphenyl}amino)ethanol, 2-({3-[(2-hydroxy-ethyl)amino]-4,5-dimethylphenyl}amino)ethanol, 2-[3-morpholin-4-ylphenyl)amino]ethanol, 3-amino-4-(2-methoxyethoxy)-5-methylphenylamine, 1-amino-3-bis-(2-hydroxyethyl)amino-benzene, resorcine, 2-methylresorcinol, 4-chlororesorcinol, 1,2,4-trihydroxybenzene, 2-amino-3-hydroxypyridine, 3-amino-2-methyl-amino-6-methoxypyridine, 2,6-dihydroxy-3,4-dimethyl-pyridine, 3,5-diamino-2,6-dimethoxypyridine, 1-phenyl-3-methylpyrazol-5-one, 1-naphthol, 1,5-dihydroxynaphthalene, 2,7-dihydroxynaphthalene, 1,7-dihydroxynaphthalene, 1,8-dihydroxynaphthalene, 4-hydroxyindole, 6-hydroxyindole, 7-hydroxyindole, 4-hydroxyindolin, 6-hydroxyindolin, 7-hydroxyindolin or mixtures of these compounds or the physiological acceptable salts thereof.

Substantive dyes may be subdivided into anionic, cationic and non-ionic substantive dyes. The substantive dyes are preferably selected from the nitrophenylene diamines, the nitro amino phenols, the azo dyes, the anthraquinones, the triarylmethane dyes or the indophenols and the physiological acceptable salts thereof If the agents include oxidation dye precursors and/or substantive dyes, then the overall amount thereof is approximately no more than 0.2% by weight, more preferably no more than 0.1% by weight and particularly preferably no more than 0.05% by weight, in relation to the overall weight of the agent ready to be applied.

As a dyeing and bleaching agent, the agents according to the invention are further characterized in that they include hydrogen peroxide and/or one of its solid attachment products on organic or inorganic compounds.

In a preferred embodiment, hydrogen peroxide itself is used as an aqueous solution. The concentration of a hydrogen peroxide solution in the agent according to the invention is determined on the one hand by legal requirements and on the other hand by the desired effect; preferably, 6 to 12% by weight of solutions in water are used. Agents of the first subject matter of the invention, which are ready to be applied and are preferred according to the invention, are characterized in that they contain, in relation to the overall weight of the agent ready to be applied, 0.5 to 20% by weight, preferably 1 to 12.5% by weight, particularly preferably 2.5 to 10% by weight and especially 3 to 6% by weight of hydrogen peroxide, in each case in relation to the overall weight of the agent.

In order to further enhance the brightening effect, at least one $SiO_2$ compound such as silicic acid or silicate, in particular water glass, may additionally be added to the composition according to the invention. According to the invention it may be preferred to use the $SiO_2$ compounds in amounts of 8.0% by weight to 20.0% by weight, particularly preferably in amounts of 10.0% by weight to 16% by weight and especially preferably in amounts of 11.0% by weight to 14.0% by weight, in each case in relation to the agent ready to be applied. The specified amounts reflect here in each case the content of the $SiO_2$ compounds (without their proportion of water) in the agents.

The dyeing agents ready to be applied may further include additional active ingredients, excipients or additives, in order to enhance the dyeing performance and in order to adjust further desired characteristics of the agents.

Agents that are suitable according to the invention may also include cationic surfactants of the types of quaternary ammonium compounds, esterquats and amidoamines. Preferred quaternary ammonium compounds are ammonium halogenides as well as the imidazolium compounds known under the INCI designations Quaternium-27 and Quatemium-83. Further cationic surfactants that can be used according to the invention are the quaternized protein hydrolysates. A compound of the amidoamines that is particularly suitable according to the invention is the stearamido-dipropylamine commercially available under the designation Tegoamid® S 18. Preferred esterquats are quaternized ester salts of fatty acids with triethanolamine, quaternized ester salts of fatty acids with diethanolalkylamines and quaternized ester salts of fatty acids with 1,2-dihydroxypropyl-dialkylamines. In the agents according to the invention, the cationic surfactants are preferably included in proportions of 0.05 to 10% by weight in relation to the overall agent.

The agents ready for application may include further excipients and additives. Thus, it has proven to be advantageous if the agents include at least one thickener. There are no principal limitations in respect of these thickeners. Both organic and purely inorganic thickeners may be used. Suitable thickeners are:

cationic, synthetic polymers;

anionic, synthetic polymers such as polyacrylates, acrylates copolymer, copolymers of acrylic acid and methacrylic acid;

naturally occurring thickeners such as non-ionic guar gums, scleroglucan gums or gum arabic, ghatti gums, karaya gums, tragacanth gums, carrageen gums, locust bean gums, pectins, xanthins, alginates, starch fractions and derivatives such as amylose, amylopectin and dextrins, as well as cellulose derivatives, such as for example carboxymethyl cellulose, methyl cellulose and hydroxyalkyl celluloses;

non-ionic, fully synthesized polymers such as polyvinyl alcohol or polyvinyl pyrrolidinone;

inorganic thickeners, in particular sheet silicates such as for example bentonite, especially smectites such as montmorillonite or hectorite.

A particularly preferred cationic polymer is Polyquaternium-4.

Bleaching and dyeing processes on keratinic fibers take place in the alkaline range. However, in order to treat the keratinic fibers and the skin as gently as possible, it is not desirable to adjust to an excessively high pH value. The pH value of the agents according to the invention may therefore be between 7.5 and 11, preferably between 9 and 10.5. The pH values in terms of the present invention may be pH values that were measured at a temperature of 22° C.

The alkalization agents that can be used according to the invention for adjusting the preferred pH value are preferably selected from ammonia, alkanolamines, basic amino acids as well as inorganic alkalization agents. Preferred inorganic alkalization agents are magnesium carbonate, sodium hydroxide, potassium hydroxide, sodium silicate and sodium metasilicate. Organic alkalization agents that can be used according to the invention are preferably selected from monoethanolamine, 2-amino-2-methyl-propanol and triethanolamine. The basic amino acids that can be used as an alkalization agent according to the invention are preferably selected from the group consisting of arginine, lysine, ornithine and histidine, particularly preferably arginine. Acidifiers that can be used for adjusting the pH value are organic acids such as citric acid, acetic acid, ascorbic acid, benzoic acid, lactic acid, malic acid and maleinic acid, as well as mineral acids such as hydrochloric acid, sulphuric acid or phosphoric acid.

It has further proven to be advantageous if the dyeing agents include at least one stabiliser or complexing agent, especially if they additionally include hydrogen peroxide. Particularly preferred stabilisers are phenacetin, alkaline benzoate (sodium benzoate) and salicylic acid. Further, all complexing agents of the prior art may be used. Complexing agents that are preferred according to the invention are nitrogen-containing polycarboxylic acids, in particular EDTA and EDDS, and phosphonates, in particular 1-hydroxyethane-1,1-diphosphonate (HEDP) and/or ethylenediamine tetramethylene phosphonate (EDTMP) and/or diethylenetriamine pentamethylene phosphonate (DTPMP) or the sodium salts thereof Further, the agents according to the invention may include further active ingredients, excipients and additives, such as for example non-ionic polymers such as for example vinylpyrrolidinone/vinyl acrylate copolymers, polyvinyl pyrrolidinone, vinylpyrrolidinone/vinyl acetate copolymers, polyethylene glycols and polysiloxanes; additional silicones such as volatile or non-volatile, straight-chained, branched or cyclic, cross-linked or non-cross-linked polyalkyl siloxanes (such as dimethicone or cyclomethicone), polyaryl siloxanes and/or polyalkylaryl siloxanes, in particular polysiloxanes with organofunctional groups, such as substituted or unsubstituted amines (amodimethicone), carboxy, alkoxy and/or hydroxyl groups (dimethicone copolyoles), linear polysiloxane(A)-polyoxyalkylene(B) block copolymers, grafted silicone polymers; cationic polymers such as quaternized cellulose ethers, polysiloxanes with quaternary groups, dimethyldiallyl ammonium chloride polymers, acrylamide-dimethyldiallyl-ammonium-chloride copolymers, diethylsulfate-quaternized dimethylamino-ethylmethacrylate vinylpyrrolidinone copolymers, vinylpyrrolidinone-imidazolinium-methochloride copolymers and quaternized polyvinyl alcohol, in particular Polyquaternium-2, Polyquaternium-4, Polyquaternium-6, Polyquaternium-7, Polyquaternium-10, Polyquaternium-11, Polyquaternium-16, Polyquaternium-24, Polyquaternium-28, Polyquaternium-37, Polyquaternium-44, Polyquaternium-46, Polyquaternium-55, Polyquaternium-67, Polyquaternium-68, Polyquaternium-69 and Polyquaternium-87; zwitterionic and amphoteric polymers such as in particular Polyquaternium-22 and Polyquaternium-39; structurants such as glucose, maleinic acid and lactic acid, hair-conditioning compounds such as phospholipids, for example lecithin and cephaline; perfume oils, dimethyl isosorbide and cyclodextrin; fiber structure improving active ingredients, in particular mono-, di- and oligo-saccharides such as for example glucose, galactose, fructose, fruit sugar and lactose; dyes for dyeing the agent; anti-dandruff active ingredients such as piroctone olamine, zinc omadine and climbazol; amino acids and oligopeptides; protein hydrolysates on an animal and/or plant basis, as well as in the form of their fatty acid condensation products or optionally anionically or cationically modified derivatives; vegetable oils; sun protection agents and UV blockers; active ingredients such as panthenol, pantothenic acid, pantolactone, allantoin, pyrrolidinone carboxylic acids and the salts thereof, as well as bisabolol; polyphenols, in particular hydroxy cinnamon acids, 6,7-dihydroxy cumarins, hydroxy benzoic acids, catechins, tannins, leucoanthocyanidins, anthocyanidins, flavanones, flavones and flavonols; ceramides or pseudoceramides; vitamins, provitamins and vitamin precursors; plant extracts; fats and waxes such as fatty alcohols, beeswax, montan wax and paraffins; bulking and penetration substances such as glycerin, propylene glycol monoethyl ethers, hydrogen carbonates, guanidins, ureas as well as primary, secondary and tertiary phosphates; opacifiers such as latex, styrene/PVP and styrene/acrylamide copolymers; pearlescent agents such as ethylene glycol mono and distearate as well as PEG-d-distearate; pigments as well as propellants such as propane butane mixtures, $N_2O$, dimethyl ether, $CO_2$ and air.

A person skilled in the art will select these further substances according to the desired properties of the agents. With regard to further optional components as well as the amounts of these components used, reference is expressly made to the relevant handbooks known to a person skilled in the art, e.g. Kh. Schrader, Grundlagen und Rezepturen der Kosmetika, 2nd Edition, Hüthig Buch Verlag, Heidelberg, 1989. The additional active ingredients and excipients are preferably used in the agents according to the invention in each case in amounts of 0.0001 to 25% by weight, in particular 0.0005 to 15% by weight, in relation to the overall weight of the mixture to be applied.

For the application of the agents according to the invention, particularly suitable is a method for dyeing keratinic fibers, in particular human hair, which is characterized in that the agent ready for application is produced by mixing differently conditioned preparations as late as just before the application. This form of application ensures that the active species responsible for the dyeing activity will not be generated until at the time of application.

In a particularly preferred form, the agent ready for application is produced by mixing two separately packaged preparations, the first preparation (preparation A) being a liquid, gel-like or creamy component that includes hydrogen peroxide. For reasons of stability, this preparation is adjusted to be slightly acidic to acidic. The second preparation (preparation B) preferably is a solid, pasty or powdery preparation that includes the persulfates (ammonium persulfate and optionally further persulfates). This preparation often includes further alkalization agents, preferably in a solid form, such as for example sodium silicates ($SiO_2:Na_2O$ in a ratio of 2:1). By mixing liquid/gel-like/creamy preparation A with solid/pasty/powdery preparation B, the agent ready for application is produced, which has an alkaline pH value.

The mixing ratio of preparations A and B may be in a range of 1:1 to 3:1 parts by weight. Particularly preferably, the mixing ratio is 2 parts by weight of preparation A to 1 part by weight of preparation B.

The agent ready for application is applied onto the keratin-containing fibers, is left on the fibers for 5 to 60 minutes and is subsequently rinsed out again with water or is washed out with a shampoo. Preferably, the contact time of the dyeing agent ready for application is 5 to 45 min, in particular 10 to 40 min, particularly preferably 15 to 35 min. During the contact time of the agent with the fibers, it may be advantageous to promote the brightening process by supplying heat. The heat supply may be carried out by means of an external source of heat, such as for example warm air from a hot air blower, as well as, in particular when brightening hair on a living test person, by the body temperature of the test person. In the latter case, the part to be brightened is usually covered with a hood. A contact phase at room temperature is also within the scope of the invention. In particular, the temperature during the contact time is between 20° C. and 40° C., in particular between 25° C. and 38° C. At the end of the contact time, the remaining dye preparation is rinsed out of the hair using water or a detergent. As a detergent, in particular commercially available shampoo may be used, and in particular if the dyeing agent has a carrier including a large amount of surfactant, the detergent may be dispensed with and the rinsing process may be carried out using water.

A further subject matter of the present invention is an agent ready for application for dyeing and/or bleaching keratinic fibers, in particular human hair, characterized in that it is produced immediately prior to the application by mixing two preparations (A) and (B), wherein preparation (A) is an agent which (a) includes arachyl alcohol (eicosan-1-ol) and/or behenyl alcohol (docosan-1-ol) in an overall amount of 0.45 to 5.1% by weight, preferably of 0.6 to 3.9% by weight, more preferably of 0.75 to 2.7% by weight and particularly preferably of 0.9 to 1.35% by weight, in relation to the overall weight of preparation (A), and (c) includes at least one compound selected from glyceryl monostearate, glyceryl distearate, glyceryl monopalmitate and glyceryl dipalmitate in an overall amount of 0.15 to 2.7% by weight, preferably of 0.3 to 2.0% by weight, more preferably of 0.4 to 1.2% by weight and particularly preferably of 0.45 to 0.9% by weight, in relation to the overall weight of preparation (A), preparation (B) is an agent that includes potassium persulfate and ammonium persulfate in an overall amount of 30 to 54% by weight, preferably of 33 to 51% by weight, more preferably of 36 to 48% by weight and particularly preferably of 39 to 45% by weight, in relation to the overall weight of preparation (B), and the agent ready to be applied is produced by mixing two parts by weight of preparation (A) with one part by weight of preparation (B).

The agents as described above are highly suitable for the comfortable dyeing of hair because they have a high dyeing performance and the user will hardly perceive the odor of the ammonia included in the agents.

Therefore, a further subject matter of the present invention is the use of the combination of (a) at least one fatty alcohol selected from the group of arachyl alcohol (eicosan-1-ol), gadoleyl alcohol ((9Z)-eicos-9-en-1-ol), arachidonic alcohol ((5Z,8Z,11Z,14Z)-eicosa-5,8,11,14-tetraen-1-ol), heneicosyl alcohol (heneicosan-1-ol), behenyl alcohol (docosan-1-ol), erucyl alcohol ((13Z)-docos-13-en-1-ol) and brassidyl alcohol ((13E)-docosen-1-ol), and (c) at least one glyceryl fatty acid ester of general formula (I),

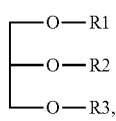

wherein
R1, R2 and R3, independently of one another, represent a hydrogen atom or a grouping of formula (II),

wherein
R4 represents an unbranched or branched, saturated or unsaturated C11-C27 alkyl group, with the proviso that at least one and no more than two of the radicals selected from R1, R2 and R3 represent a grouping of formula (II),
for reducing the ammonia odor in dyeing agents including in a cosmetic carrier (b) ammonium persulfate as well as optionally a further persulfate salt.

What was said in relation to the agents according to the invention also applies, mutatis mutandis, to further preferred embodiments of the method and use according to the invention.

1. Formulation Examples

The following compositions were prepared. Unless otherwise specified, the amounts indicated are in each case to be understood in percent by weight.

Preparation A

| Formulation Components | (% by weight) |
| --- | --- |
| Cetaryl alcohol | 3.70 |
| Behenyl alcohol (docosan-1-ol) | 1.10 |
| Paraffinium Liquidum | 0.65 |
| Ceteareth-30 ($C_{16}$-$C_{18}$ fatty alcohols, ethoxylated with 30 EO) | 0.50 |
| Cutina GMS-V (mixture of glyceryl monostearate, glyceryl distearate, glyceryl monopalmitate and glyceryl dipalmitate) | 0.50 |
| Hydroxyethane-1,1-diphosphonic acid | 0.15 |
| Propylene glycol | 0.50 |
| Cocamidopropyl betain | 0.12 |
| Disodium pyrophosphate | 0.18 |
| Phenoxyethanol | 0.20 |
| Sodium benzoate | 0.10 |
| Hydrogen peroxide (50% aqueous solution) | 12.00 |
| Water | Ad 100 |

Preparation B

| Formulation components | (% by weight) |
| --- | --- |
| Sodium silicate ($SiO_2$:$Na_2O$ = 2:1) | 36.00 |
| Magnesium carbonate | 12.85 |
| Sodium hexametaphosphate | 0.20 |
| Rohagit S hv (methyl methacrylate, methacrylic acid copolymer) | 1.00 |
| EDTA disodium salt (ethylene diamine tetra acetic acid, disodium salt) | 0.60 |
| Polyquaternium-4 | 0.30 |
| Silicic acid, hydrophilic | 0.40 |
| Glycine | 0.60 |
| Potassium persulfate | 32.00 |
| Ammonium persulfate | 10.00 |
| Ariabel Blue 300302 (CI 77007 (ULTRAMARINES) | 0.15 |
| Dimeticone, Dimethiconole | 1.50 |
| Paraffinium Liquidum | 3.80 |

For the production of the agent ready for application, 2 parts by weight of preparation A were mixed with one part by weight of preparation B.

While at least one exemplary embodiment has been presented in the foregoing detailed description of the invention, it should be appreciated that a vast number of variations exist. It should also be appreciated that the exemplary embodiment or exemplary embodiments are only examples, and are not intended to limit the scope, applicability, or configuration of the invention in any way. Rather, the foregoing detailed description will provide those skilled in the art with a convenient road map for implementing an exemplary embodiment of the invention, it being understood that various changes may be made in the function and arrangement of elements described in an exemplary embodiment without departing from the scope of the invention as set forth in the appended claims and their legal equivalents.

What is claimed is:

1. An agent ready to be applied for dyeing and/or bleaching keratinic fibers, and that it is produced immediately prior to application by mixing two preparations (A) and (B), wherein:

preparation (A) is an agent which includes components (a) and (c), wherein component (a) includes at least one fatty alcohol selected from the group consisting of arachyl alcohol (eicosan-1-ol), gadoleyl alcohol ((9Z)-eicos-9-en-1-ol), arachidonic alcohol ((5Z,8Z,11Z,14Z)-eicosa-5,8,11,14-tetraen-1-ol), heneicosyl alcohol (heneicosan-1-ol), behenyl alcohol (docosan-1-ol), erucyl alcohol ((13Z)-docos-13-en-1-ol) and brassidyl alcohol ((13E)-docosen-1-ol) in an overall amount of 0.45 to 5.1% by weight, in relation to the overall weight of preparation (A), component (c) includes at least one glyceryl fatty acid ester of general formula (I),

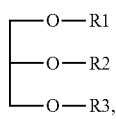

(I)

wherein
R1, R2 and R3, independently of one another, represent a hydrogen atom or a grouping of formula (II),

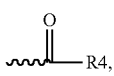

(II)

wherein
R4 represents an unbranched or branched, saturated or unsaturated C11-C27 alkyl group, with the proviso that at least one and no more than two of the radicals selected from R1, R2 and R3 represent a grouping of formula (II) in an overall amount of 0.15 to 2.7% by weight in relation to the overall weight of preparation (A), and preparation (B) is an agent that includes component (b), wherein component (b) includes at least one persulfate salt including ammonium persulfate in an overall amount of 30 to 54% by weight in relation to the overall weight of preparation (B), and the agent ready to be applied is produced by mixing two parts by weight of preparation (A) with one part by weight of preparation (B).

2. The agent according to claim 1, wherein the fatty alcohol(s) include (a) arachyl alcohol (eicosan-1-ol) and/or behenyl alcohol (docosan-1-ol) in an overall amount of 0.3 to 3.4% by weight, in relation to the overall weight of the agent when ready for application.

3. The agent according to claim 1, wherein the overall amount of all the fatty alcohols included in the agent, in relation to the overall weight of the agent when ready to be applied, does not exceed an amount of 5.5% by weight.

4. The agent according to claim 1, wherein the at least one persulfate salt (b) further includes potassium persulfate, and wherein the potassium persulfate and the ammonium persulfate are included in an overall amount of 10 to 18% by weight in relation to the overall weight of the agent when ready to be applied.

5. The agent according to claim 4, wherein the weight ratio between potassium persulfate and ammonium persulfate is in a range of 1:1 to 6:1 in relation to the overall weight of the agent when ready to be applied.

6. The agent according to claim 1, wherein the glyceryl fatty acid esters (c) of general formula (I) include at least one compound selected from the group consisting of glyceryl monostearate, glyceryl distearate, glyceryl monopalmitate and glyceryl dipalmitate in an overall amount of 0.1 to 1.8% by weight in relation to the overall weight of the agent when ready to be applied.

7. The agent according to claim 1, further including one or more amphoteric and/or zwitterionic surfactants in an overall amount of 0.01 to 0.5% by weight in relation to the overall weight of the agent when ready to be applied.

8. The agent according to claim 1, characterized in that it includes, in relation to the overall weight of the agent ready to be applied, less than 0.5% by weight anionic surfactants.

9. The agent according to claim 1, further including one or more ethoxylated fatty alcohols of formula (III),

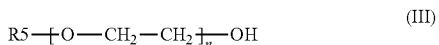

(III)

wherein R5 represents an unbranched or branched, saturated or unsaturated C12-C28 alkyl group, and n represents an integer of 25 to 120.

10. An agent ready to be applied for dyeing and/or bleaching keratinic fibers, characterized in that it is produced immediately prior to application by mixing two preparations (A) and (B), wherein preparation (A) is an agent which
(a) includes arachyl alcohol (eicosan-1-ol) and/or behenyl alcohol (docosan-1-ol) in an overall amount of 0.45 to 5.1% by weight, in relation to the overall weight of preparation (A), and (c) includes at least one compound selected from the group consisting of glyceryl monostearate, glyceryl distearate, glyceryl monopalmitate and glyceryl dipalmitate in an overall amount of 0.15 to 2.7% by weight in relation to the overall weight of preparation (A), preparation (B) is an agent that includes potassium persulfate and ammonium persulfate in an overall amount of 30 to 54% by weight in relation to the overall weight of preparation (B), and the agent ready to be applied is produced by mixing two parts by weight of preparation (A) with one part by weight of preparation (B).

* * * * *